(12) United States Patent  
Fogarty et al.

(10) Patent No.: US 6,299,621 B1
(45) Date of Patent: Oct. 9, 2001

(54) SURGICAL CLAMP PADS WITH ELASTOMER IMPREGNATED MESH

(75) Inventors: Thomas J. Fogarty; George D. Hermann, both of Portola Valley; Joshua S. Whittemore, Mountain View; Thomas A. Howell, Palo Alto, all of CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 0 days.

(21) Appl. No.: 09/336,018

(22) Filed: Jun. 18, 1999

(51) Int. Cl.[7] ................................................ A61B 17/04
(52) U.S. Cl. .................... 606/151; 606/157; 606/158; 606/207
(58) Field of Search ..................... 606/205–207, 606/151, 157, 158

(56) References Cited

U.S. PATENT DOCUMENTS

| | | | |
|---|---|---|---|
| 2,743,726 | * 5/1956 | Grieshaber | 128/321 |
| 3,503,396 | * 3/1970 | Pierie et al. | 128/322 |
| 3,503,397 | * 3/1970 | Fogarty et al. | 128/322 |
| 3,503,398 | * 3/1970 | Fogarty et al. | 128/346 |
| 3,663,973 | * 5/1972 | Spence | 5/665.5 |
| 3,719,963 | * 3/1973 | Bullock, Jr. | 264/45.5 |
| 3,746,002 | 7/1973 | Haller | 128/322 |
| 3,880,166 | * 4/1975 | Fogarty | 128/325 |
| 3,993,076 | 11/1976 | Fogarty | 128/325 |
| 4,545,202 | 10/1985 | Duncan | 128/334 |
| 4,611,593 | 9/1986 | Fogarty et al. | 128/325 |
| 4,821,719 | 4/1989 | Fogarty | 128/325 |
| 4,955,897 | 9/1990 | Ship | 606/210 |
| 5,171,253 | 12/1992 | Klieman | 606/158 |
| 5,535,756 | 7/1996 | Parasher | 136/756 |
| 5,591,182 | 1/1997 | Johnson | 606/151 |
| 5,882,833 | 5/1976 | Schulte et al. | 128/20 |
| 6,007,552 | 12/1999 | Fogarty et al. | 606/157 |

FOREIGN PATENT DOCUMENTS

| | | | |
|---|---|---|---|
| 65626 | 9/1919 | (CH) . | |
| 0 490 301 A1 | 12/1991 | (EP) | A61B/17/28 |
| WO 99/11179 | 9/1997 | (WO) | A61B/17/08 |
| WO 99/30683 | 12/1997 | (WO) | A61B/17/122 |
| WO 98/33437 | 8/1998 | (WO) | A61B/17/00 |

* cited by examiner

Primary Examiner—Gary Jackson
(74) Attorney, Agent, or Firm—Morrison & Foerster LLP

(57) ABSTRACT

Replaceable pads are provided for jaw-type surgical clamps, clips and other occluding devices. The pads include elastomer impregated mesh embedded in and extending from an elastomeric cushion. When engaged with a vessel, the mesh partially penetrates the adventitial layers of the vessel, securing outer adventitial layers against inner vessel layers to resist relative movement of the layers, thereby minimizing slippage of the device along the clamped vessel. The embedded mesh also functions to stabilize the cushion, especially against lateral movement.

42 Claims, 8 Drawing Sheets

SURGICAL CLAMP PADS WITH ELASTOMER IMPREGNATED MESH

BACKGROUND OF THE INVENTION

The present invention relates generally to surgical instruments for occluding a vessel. More particularly, the invention relates to surgical instruments such as surgical clamps and other occlusion devices, and to replaceable clamp pads for attachment to such instruments, that provide for improved atraumatic occlusion of such vessels.

Instruments for occluding blood vessels during surgery, such as conventional metal or rigid surgical clamps or clips, are well known. However, such instruments are known to cause trauma to the clamped vessel at the clamping site. A number of atraumatic instruments have been developed for reducing or eliminating the trauma to a vessel during occlusion of the vessel. U.S. Pat. No. 3,993,076 to Fogarty, et al. describes a device whereby a vessel is occluded by using a resilient tape to press a vessel against a resilient pad. However, this device suffers from the disadvantage that it slips easily and can be cumbersome to use. For example, the pulsations of an occluded artery can tend to force the device off of its clamped position on the occluded artery. Conventional surgical clamps have also been adapted to include jaw surfaces containing resilient members or pads. These devices likewise are prone to slipping off of the clamped vessel. This can be especially problematic in situations where, due to obstructions, a vessel has been clamped with only the distal tips of the clamp jaws. In such situations, the vessel can be especially prone to slipping in the direction of the distal tips.

Of particular difficulty in preventing slippage of an engaged clamp along a clamped vessel is the nature of blood vessels themselves. Blood vessels generally consist of an inner endothelial layer, an intermediate layer of smooth muscle, and an outer layer of adventitia that is composed primarily of fibrous connective tissue. The connective tissue in the adventitia itself is organized into a series of layers with the innermost layer having denser, more closely packed connective tissue and outer layers gradually becoming looser and less densely packed. These outermost layers of adventitia under sufficient force or pressure can move relative to inner vessel layers, much like the movement of an outer sleeve over an inner sleeve. As a result, a surgical clamp engaged with and contacting the outer adventitial layer can slip along the vessel by virtue of the movement of the engaged outer adventitial relative to the inner layers. With increased clamping force, such slippage can be minimized but such additional force often leads to trauma to the vessel itself.

Other attempts have been made to atraumatically occlude a vessel in a secure fashion. U.S. Pat. No. 3,746,002 to Haller describes a vascular clamp with resilient gripping members located on the jaws. A plurality of pin members are embedded within the gripping members, the pin members of a length such that when a vessel is clamped between the members, the resilient material deflects to accommodate the vessel, exposing the pin members which grippingly engage the outer layer of the vessel, thus securing the vessel to the gripping member. While the Haller device is less traumatic to a vessel than other occlusion devices, it nevertheless has the disadvantage of traumatizing the outer layer of the vessel, as the pins are rigid and non-conforming to the vessel.

U.S. Pat. No. 4,821,719 to Fogarty describes a vascular clamp device containing resilient pads with Velcro-like hooks. The hooks interact with the external adventitial layer of the vessel forming a cohesive-adhesive relationship with the vessel similar to the bonding of Velcro materials. While this device offers a less traumatic way to occlude a vessel, the cohesive-adhesive nature of the bond can result in the removal of some of the adventitial layer of the vessel when disengaging the device. Also, slippage can still occur between the engaged adventitia and the inner vessel layers. Applied Medical (Laguna Hills, Calif.) manufactures a clamp pad under the tradename A-TRAC that contains a mesh surface layered over a soft cushion.

Still other efforts have been made to provide improved clamping of vessels while resisting movement. Our own U.S. application Ser. No. 08/993,076, filed Dec. 18, 1997, describes surgical clamps with resilient filaments extending from gripping surfaces. The filaments terminate in free distal ends that abut against the engaged vessel to restrict movement relative to the filament orientation. PCT International Publication No. WO 98/33437 describes other methods of increasing the traction force applied to a clamped vessel, including the use of bristles that axially crumple to develop an occlusive force and that resist movement of the vessel relative to the instrument. The column strength of each bristle provides traction in a predetermined direction.

Despite these advances, there remains a need for a surgical clamp having clamping pads or regions which atraumatically occlude vessels while avoiding the disadvantages previously associated with existing surgical clamps or occlusion devices, including pads that miminize slippage that occurs as a result of the relative movement between outer adventitia and inner vessel layers.

SUMMARY OF THE INVENTION

The present invention meets these and other needs and provides for a pad or member that is attachable to the jaw of a jaw-type occlusion device, such as a surgical clamp or clip. The pad includes an elastomeric cushion with a woven mesh embedded in the cushion. A portion of the mesh is exposed at the clamping surface of the cushion for engagement with a clamped vessel. The mesh in this portion is itself impregnated with an elastomeric material such that a continuous sheet is formed comprised of interwoven mesh fibers encapsulated in elastomeric material. The elastomeric material spanning the fibers forms a web therebetween. The individual fibers of the mesh are themselves preferably resiliently deflectable and are generally stiffer and less easily deflected than both the elastomeric material spanning the fibers and the elastomeric cushion.

When a pad according to the invention engages a blood vessel, the configuration of the elastomer impregnated mesh allows for partial penetration of the mesh into the adventitial layers of the vessel. While not being bound by theory, we believe that as the mesh moves through the looser, outermost layers of adventitia it encounters deeper layers that are dense enough to provide resistance to further penetration by the mesh. Further advancement of the mesh compresses these layers against the inner vessel layers, thereby in essence pinning these layers against the inner layers and resisting movement of the outer adventitia relative to the inner vessel layers. However, as both the fibers and elastomeric material comprising the mesh are resiliently deflectable, the securing effect of the mesh is accomplished with the minimum of trauma to the adventitia and underlying vessel tissue.

In addition, the characteristics of the cushion and the embedded mesh are such that the cushion and mesh work together to achieve a synergistic effect. The portion of the cushion containing the embedded mesh forms a clamping region of the cushion. The embedded mesh provides structural support to the clamping region by reinforcing and stabilizing the region against deformation, especially lateral deformation, when the pad is under a clamping load. The clamping region in turn stabilizes and orients the mesh at the desired angle relative to the cushion surface. The clamping region performs this orientation function prior to and during the application of a clamping load to the pad. When a load is applied to the pad, the mesh and the cushion are deflected, but the clamping region stabilizes the mesh against excessive deformation and maintains the desired orientation of the mesh. The clamping region continues to perform this function as the load is released from the pad and the deflected mesh and cushion return to their original pre-loaded positions.

Methods of manufacturing the attachable pads or members of the present invention are also provided. In one method, a folded sheet of mesh or a cylindrical sleeve of mesh is provided and secured in a mold. The mold is then filled with a liquid elastomeric material that is allowed to harden, forming a resilient cushion around the mesh as well as impregnating the mesh itself with the elastomeric material. The impregnated mesh extending from the cushion is then cut at the desired height above the cushion surface. In a second method, one or more preformed sheets of elastomer impregnated mesh are provided and the elastomeric cushion of the pad is formed around the sheets such that the formed cushion contains mesh embedded longitudinally along the cushion. The sheets themselves can be embedded at varying angles relative to the cushion surface. Again, the mesh extending from the cushion surface can further be cut at the desired height above the cushion surface.

DETAILED DESCRIPTION OF THE INVENTION

Figure 1A:
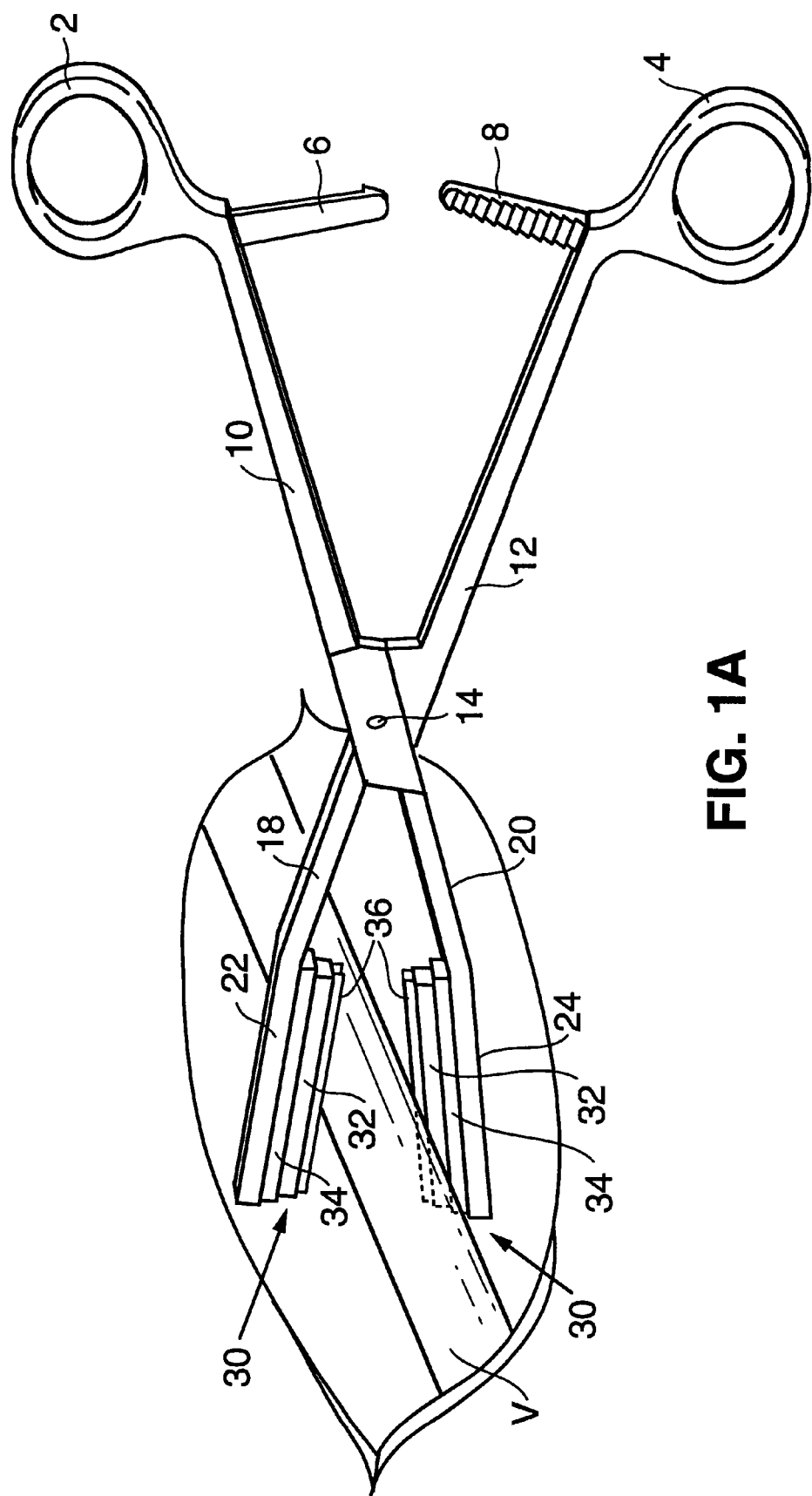
FIG. 1A is a perspective view of a surgical clamp according to the present invention in a position to engage a vessel.
Figure 1B:
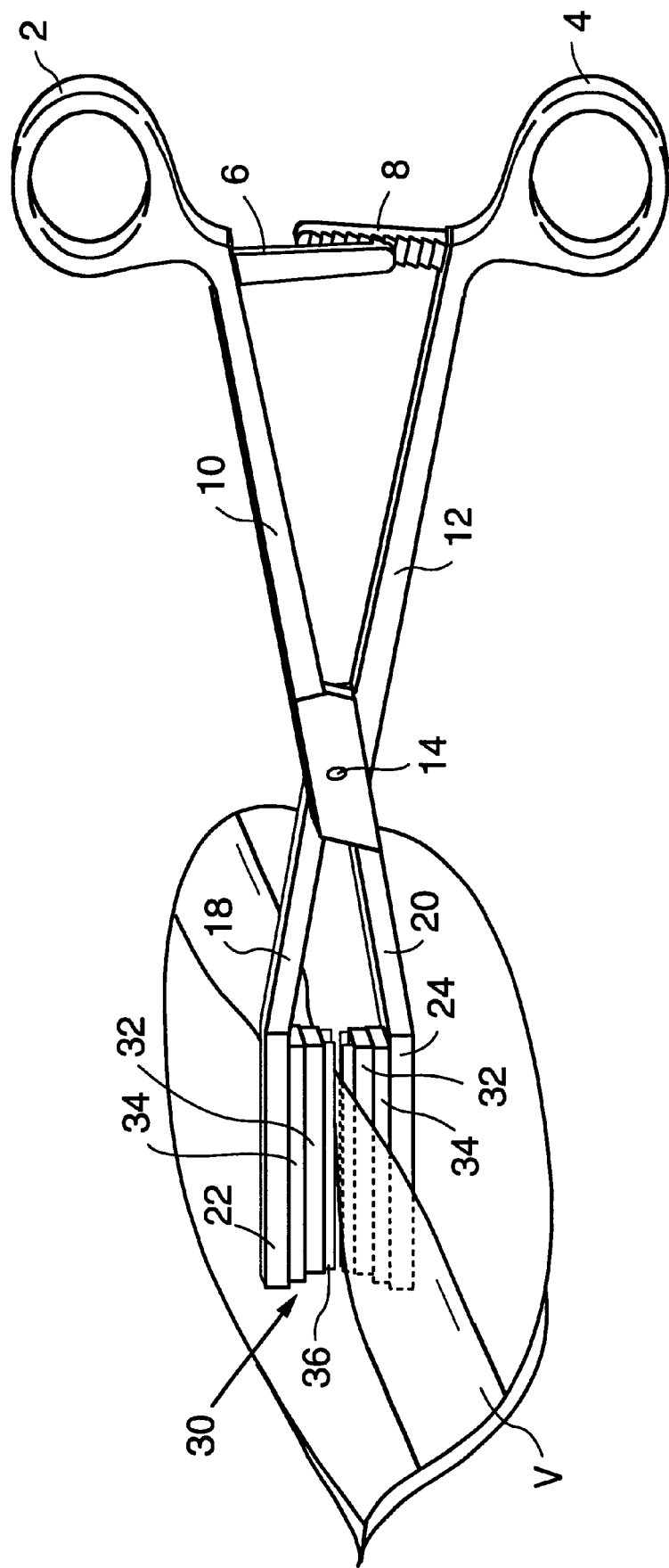
FIG. 1B is a perspective view of the surgical clamp of FIG. 1A engaged with and occluding a vessel.

FIG. 1A shows a surgical clamp comprising a pair of opposed jaws 22 and 24 and handles 10 and 12 hinged together by pin 14. The handles 10 and 12 terminate in finger and thumb rings 2 and 4 that provide for manual operation of the jaws by a surgeon. Interlocking pawl 6 and ratchet teeth 8 are provided on handles 10 and 12, respectively, to secure jaws 22 and 24 in an adjusted clamped position with a vessel V. In FIG. 1A, opposed jaws 22 and 24 are positioned to engage vessel V. Attached to each jaw are pads 30, 30. Each pad 30 includes an elastomeric cushion 32 secured to attaching member 34, which is in turn detachably secured to one of the jaws. Elastomer-impregnated mesh 36 is embedded into each cushion 32 with a portion of the mesh extending from the surface of each cushion. FIG. 1B shows the surgical clamp in an adjusted clamped position. The opposed pads 30, 30 have engaged and clamped down upon vessel V, thereby causing occlusion of vessel V. Interlocking ratchet teeth 8 are engaged with interlocking pawl 6 to secure the opposed jaws in the clamped position. While FIGS. 1A and 1B depict surgical clamp pads according to the present invention used with a typical jaw-type surgical clamp, the invention also contemplates the adaptation of the inventive pads for use with other occlusion devices known in the art, including surgical spring clips and the like.

The elastomer-impregnated mesh 36 is formed of flexible woven fibers, the fibers themselves preferably being resiliently deflectable. Preferred materials for the mesh fibers include nylon, polyester or polypropylene. The mesh is impregnated with a thin film of elastomer, preferably a silicone, vinyl or thermoplastic elastomer, which spans the spaces between the individual woven fibers of the mesh to form a web between the fibers. The preferred thickness of the fibers is 0.005 to 0.012 inches, preferably 0.007 inches. Wider filaments may be used, provided they are sufficiently flexible. The resulting mesh has the characteristics of a continuous sheet that is flexible yet resilient. The overall thickness of this sheet is slightly thicker than the thickness of the individual fibers due to the addition of the elastomer film.

Elastomeric cushion 32 can be formed of a variety of materials known in the art that are resiliently deflectable and provide cushioning to a clamped vessel. The preferred material is a silicone, most preferably a two part silicone of less than a 50 durometer shore A, liquid injection moldable (GE 6040) or a silicone foam such as GE RTF762. Thermoplastic elastomers, such as polyurethane or KRATON® (Shell Chemicals Ltd.), are also suitable.

As shown in FIGS. 1A and 1B, mesh 36 is embedded longitudinally in cushion 32. The fibers of the mesh terminate in distal ends spaced from the cushion surface, the ends being exposed through the elastomer and coterminous with the elastomer web. While this is the preferred orientation of the mesh relative to the cushion length, other orientations are contemplated, provided they result in a portion or portions of mesh extending from the cushion surface for engagement with a vessel. Similarly, the embodiment of FIGS. 1A and 1B shows two separate lengths of mesh 36 extending from the surface of cushion 32, but a single or multiple lengths can also be effectively used.

Attaching member 34 provides a rigid backing for cushion 32 and means for attachment of cushion 32 to opposed jaws 22 and 24. The member 34 can be made of a hard plastic, such as polycarbonate, or of metal. Means for attaching member 34 to opposed jaw 22 or 24 can comprise a pair of protrusions (not shown) detachably coupled to recesses on the jaw (not shown). Other conventional means may also be employed. In an alternative embodiment, the cushion can be directly secured to a jaw of a clamp by means described in copending U.S. application Ser. No. 09/336,131 entitled "Surgical Clamp Having Replaceable Pad," filed Jun. 18, 1999, commonly owned by the assignee of the present application and incorporated herein in its entirety.

Figure 2A:
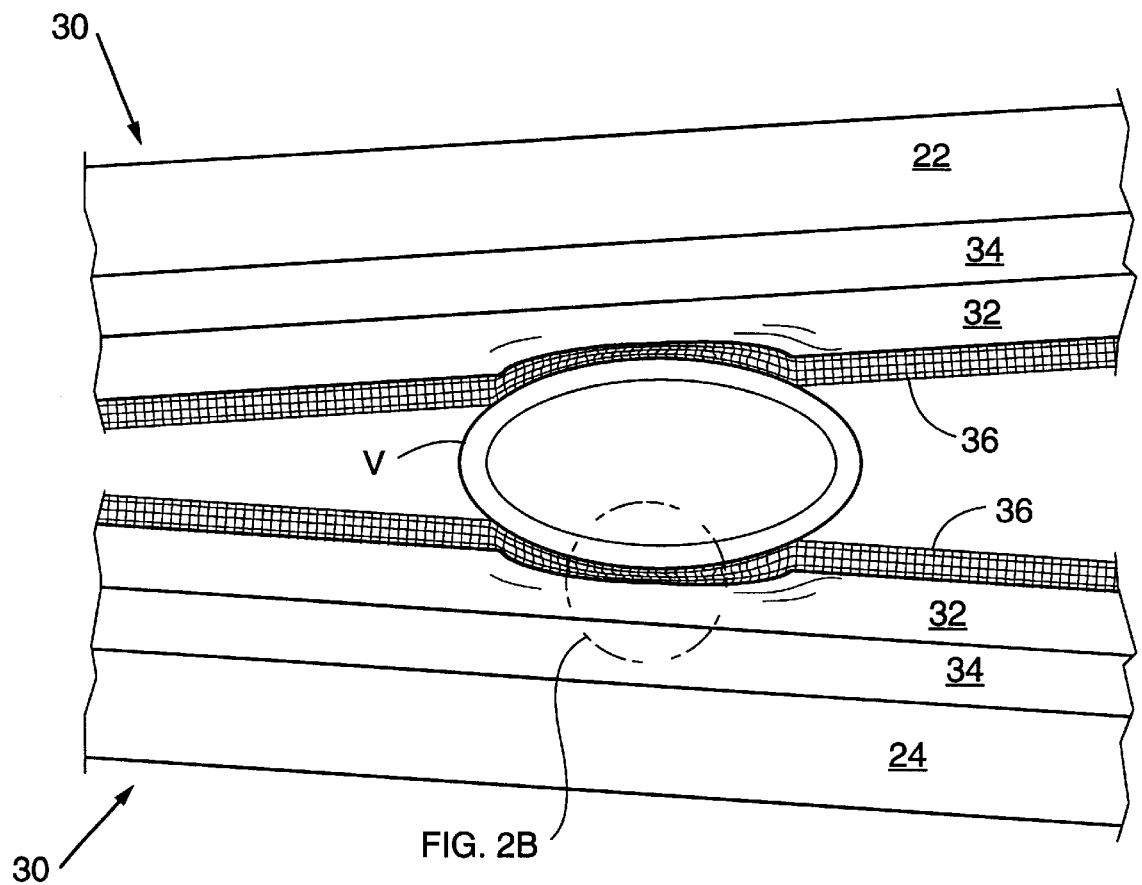
FIG. 2A is a side view of opposed jaws of a surgical clamp according to the present invention with attached clamp pads containing elastomer impregnated mesh where the pads have engaged the vessel and the vessel is partially occluded.
Figure 2B:
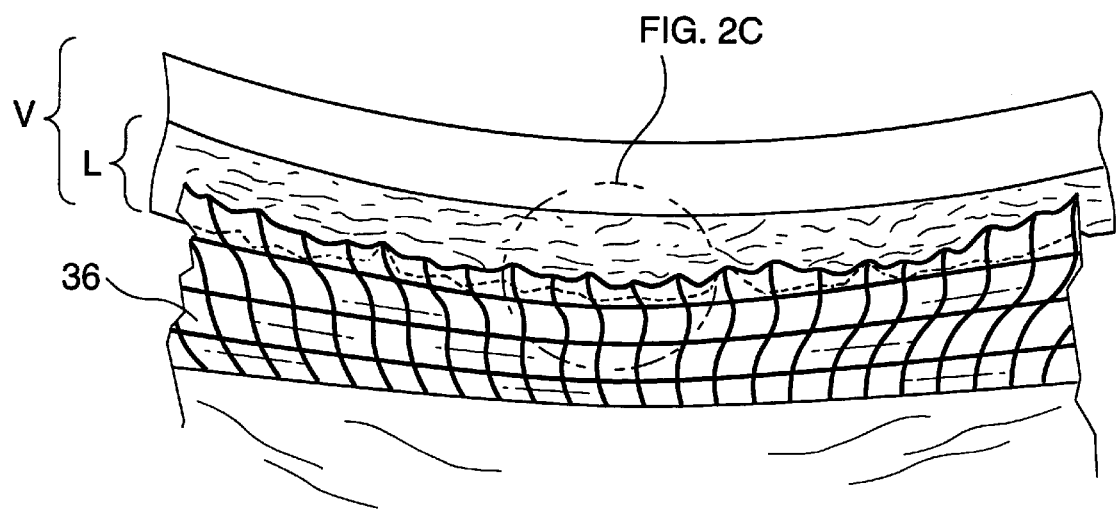
FIG. 2B is an enlarged view of the circled portion 2B of FIG. 2A, showing the mesh engaged with the vessel.
Figure 2C:
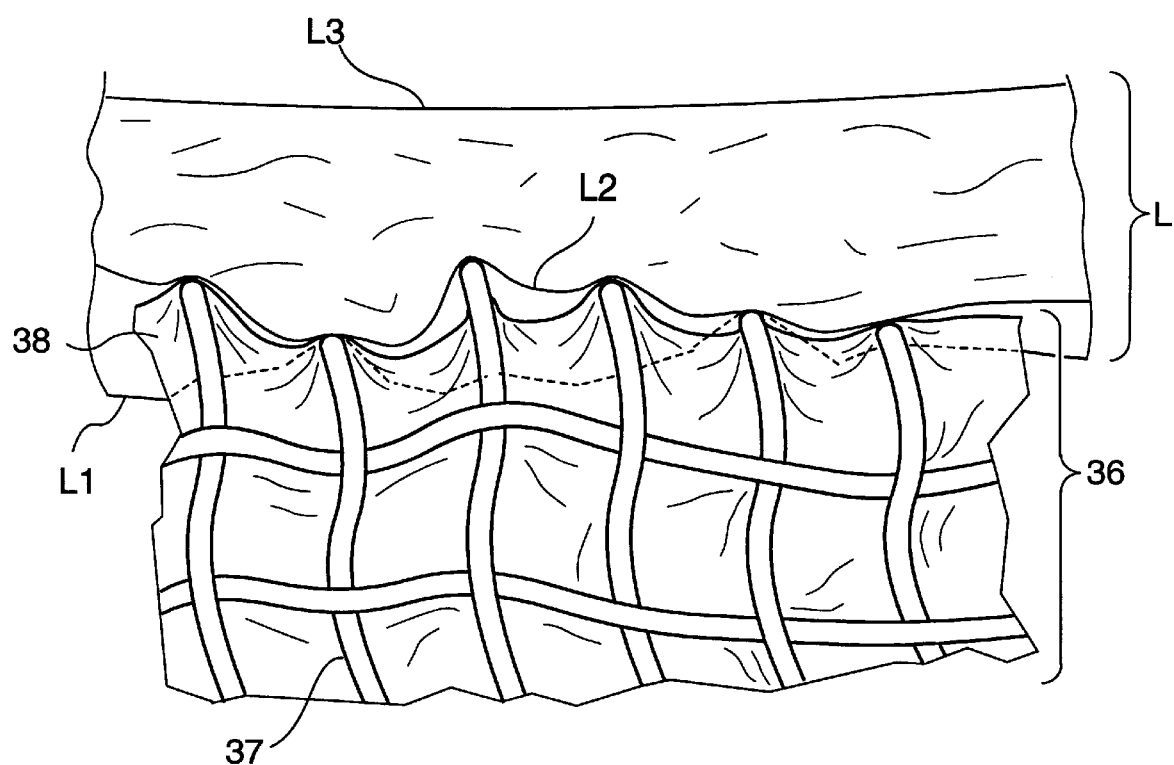
FIG. 2C is an enlarged view of the circled portion 2C of FIG. 2B, showing the mesh engaged with the vessel.

The operation of one embodiment of the invention is depicted in FIGS. 2A–2C. FIG. 2A illustrates opposed jaws 22 and 24, each including pad 30, in partial engagement with vessel V. The interaction of the pad 30 with the engaged vessel V is depicted in greater detail in FIGS. 2B and 2C. As depicted in FIGS. 2A and 2B, elastomeric cushion 32, which is generally softer and more easily deflectable than elastomer impregnated mesh 36 deflects to accommodate the general shape of vessel V, helping minimize trauma to engaged vessel V. Mesh 36 also partially deflects upon engagement with vessel V, as shown more clearly in FIGS. 2B and 2C, further minimizing trauma to the vessel. At the same time, however, the mesh is stiff enough to partially penetrate the loose, outermost adventitial layers L1. As the mesh encounters denser adventitial layers L2 it reaches a point where it can no longer penetrate through these layers, and the mesh then compresses and pushes these layers against inner vessel layers L3. In this manner, the vessel is occluded with minimum damage to the vessel while the outer adventitial layers are secured against the inner vessel layers, thereby restricting movement of the adventitia, and thus pad 30 itself, relative to the engaged vessel.

As seen in greater detail in FIG. 2C, fibers 37 that comprise mesh 36 are themselves resiliently deflectable, but are stiffer and less deflectable than the elastomeric film 38 that impregnates the mesh. Elastomeric film 38 stretches and deflects to accommodate both the engaged adventitial layers and the deflected fibers 37. The degree of deflection of both the fibers and the elastomer is dependent upon a number of factors, including the overall load placed on the pad as well as localized characteristics of the engaged vessel itself. For example, within the vessel layers themselves, there may be regions that are more or less susceptible to compression, and which will thus affect the degree of deflection of both the fibers and elastomer at the particularly engaged region. As can be seen in FIG. 2C, under certain conditions of load and/or localized resistance, the elastomer may deflect to such a degree that some of the distal tips of the fibers are exposed while elsewhere fiber tips are not exposed. At the same time, the general tendency of the elastomer to adhere to the fibers ensures that the fiber tips are not exposed to such an extent that they risk deeply penetrating and traumatizing the vessel. This results in a continuous and dynamic interaction of mesh with retained adventitia that adjusts to varying localized conditions during clamping.

The overall result is that the combination of fibers and elastomer film provides for continuous securing of outer adventitial layers against inner vessel layers, all along the length of mesh 36. The elastomer film provides for continuous or near-continuous contact with the retained adventitia along the length of the mesh while the mesh fibers provide structural support for the elastomer film. While FIGS. 2B and 2C depict mesh 36 having fibers oriented at generally right angles relative to the cushion surface, it is to be understood that any orientation of mesh fibers will achieve the desired effect.

The elastomer impregnated mesh also provides for increased stability of cushion itself. As previously described, and as further shown by the embodiments depicted in FIGS. 13 and 14, a portion of the mesh is embedded in the cushion. In preferred embodiments, the cushion material is softer and more easily deflected than the fibers of the mesh. The stiffer mesh fibers function to reinforce and stabilize the cushion, making it more resistant to deformation. In turn, the cushion orients and stabilizes the mesh in the desired position relative to the cushion surface. In cases where the mesh is embedded longitudinally along the length of the cushion, as shown for example in FIGS. 13 and 14, the embedded portion of the mesh especially functions to resist lateral deformation of the cushion. Further, while the cushions of FIGS. 13 and 14 include mesh that both reinforces the cushion and extends from the cushion surface, the present invention also contemplates a mesh reinforced cushion having a conventional engaging surface with reinforcing mesh embedded entirely within the cushion. Such a cushion would likewise be especially resistant to lateral deformation. This resistance to lateral deformation is not present in clamp pads that otherwise consist primarily of a gripping surface which is layered over an underlying cushioned material, such as, for example, the pad described in U.S. U.S. Pat. No. 4,821,719.

The manufacture of pads according to the present invention can be accomplished in many ways, as will be apparent to one skilled in the art. In a preferred method, the elastomeric cushion is formed from a curable polymeric material, such as an injection moldable silicone, elastomer foam, or thermoplastic elastomer (e.g., polyurethane, KRATON®) that is allowed to cure with the mesh in the desired position, resulting in the embedding of a portion of the mesh within the cushion. The mesh can be provided already impregnated with elastomeric material, i.e., preformed impregnated mesh. Alternatively, non-impregnated mesh can be provided and the impregnation of the mesh with elastomeric material can occur during the manufacturing process itself.

Figure 3:
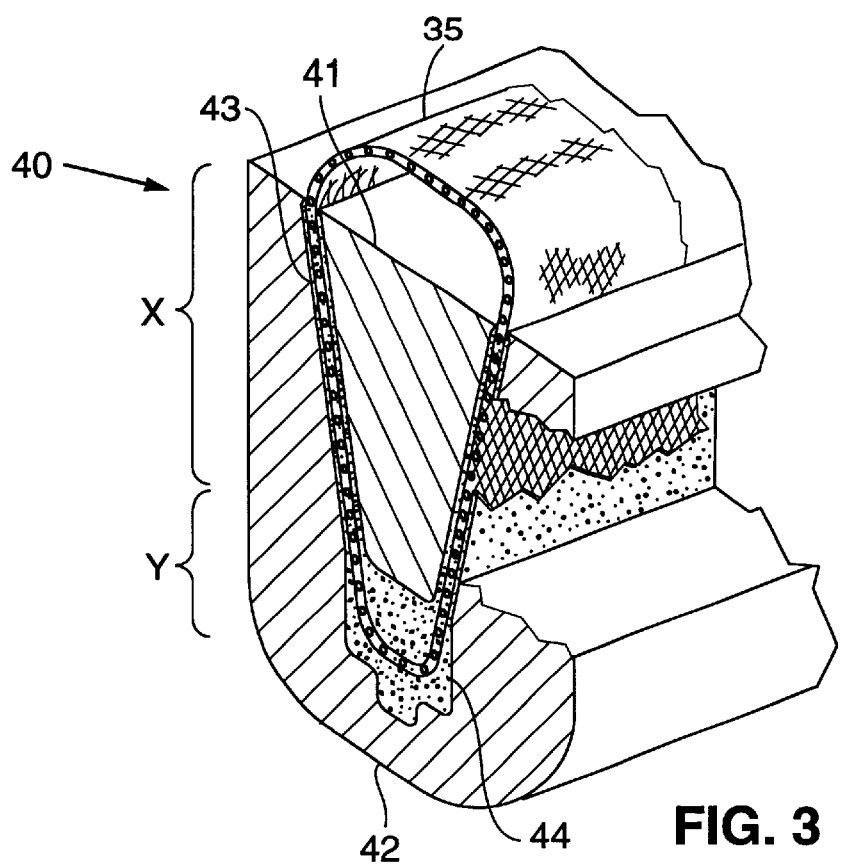
FIG. 3 is a perspective view with a partial cut-away showing a tubular sleeve of woven mesh secured in a mold and elastomeric material in the mold space.
Figure 4:
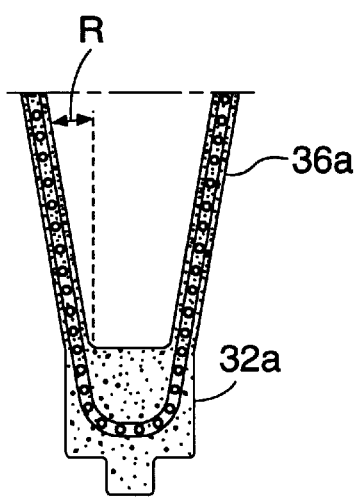
FIG. 4 is an end view of a cushion according to the present invention constructed through the use of the FIG. 3 mold.
Figure 5:
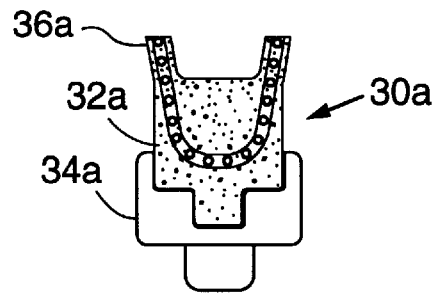
FIG. 5 is an end view of the FIG. 4 cushion secured to an attaching member.
Figure 6:
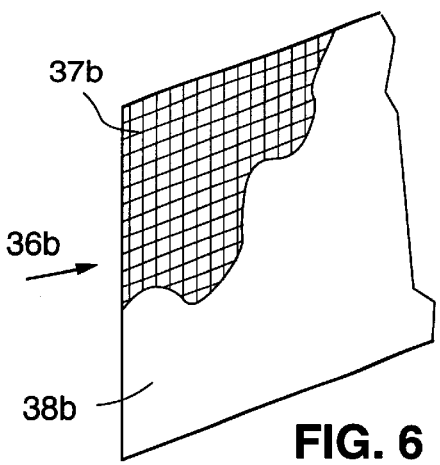
FIG. 6 is a perspective view of an elastomer impregnated sheet of woven mesh.
Figure 7:
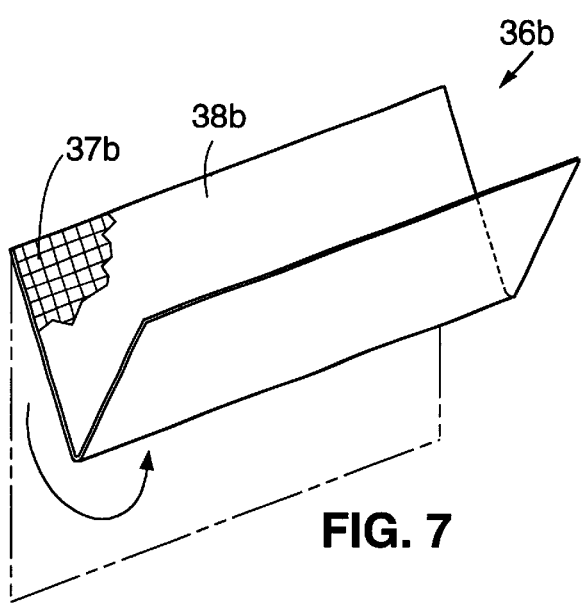
FIG. 7 is a perspective view of the sheet of FIG. 6 showing the sheet folded.
Figure 8:
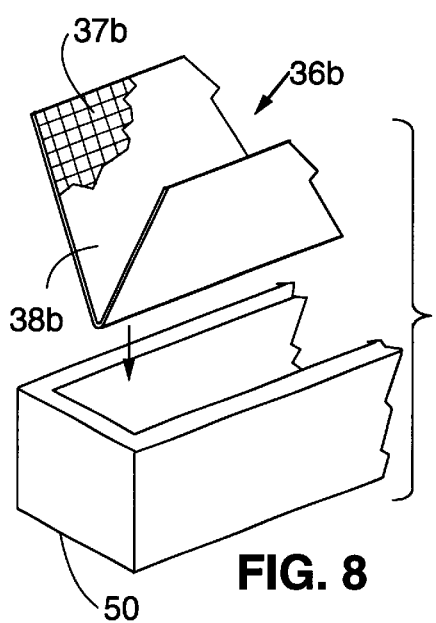
FIG. 8 is a perspective view of the folded sheet of FIG. 7, showing the folded sheet being inserted into a mold.
Figure 9:
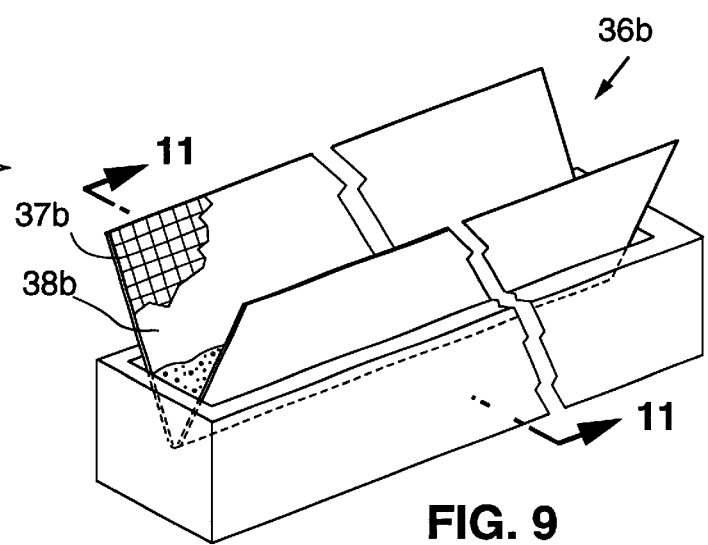
FIG. 9 is a perspective view of the folded sheet and mold assembly of FIG. 8 with elastomeric material filling the mold space.

A preferred method of manufacture is depicted in FIGS. 3–5. In this method, a tubular sleeve of woven mesh 35 is secured within mold 40 having upper and lower portions 41 and 42. An elastomer, such as silicone or silicone foam, is then injected into the mold and allowed to cure, securing the mesh 35 to the formed cushion 32a. Ideally, the mesh will extend through most, if not all, of the cushion depth. As depicted in FIG. 3, the mold space is configured to provide a narrow channel 43 contiguous with the sleeve that forms an upper web forming section X of the mold and a larger channel 44 corresponding to the desired pad dimensions that forms a lower cushion forming section Y of the mold. The elastomer fills these channels, covering and impregnating the mesh with elastomer in the web forming section. Upon hardening, the elastomer forms a thin elastomeric film around the mesh in this section. The formed cushion 32a with elastomer-impregnated mesh 36a is then removed from mold 40. The mesh is then cut at the desired height above the cushion surface, as shown in FIG. 5, so that the ends of the fibers are coterminous with the web of mesh reinforced elastomer. In the preferred embodiment, the mesh extends about 0.05 inches above the cushion surface. In the embodiment depicted in FIG. 4, the mesh extends outward at an angle R from vertical relative to the cushion surface. The preferred angle is between 0–20 degrees from vertical, angled either away from or toward the pad center. The cushion is then bonded or otherwise secured to attaching member 34a, as shown in FIG. 5, to form the finished pad 30b. Again, it is preferable that the formed elastomer impregnating the mesh is of a softer resiliency than that of the individual mesh fibers themselves.

Figure 12:
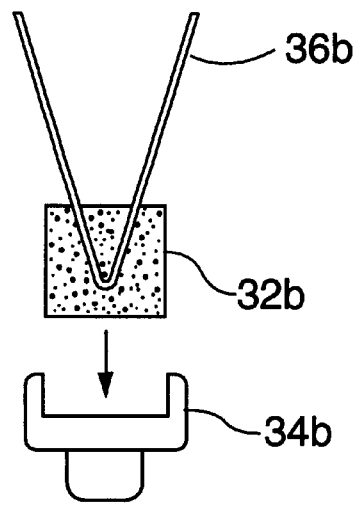
FIG. 12 is an end view of the assembly of FIG. 10 positioned for securement to an attaching member.

Another method of manufacture using preformed elastomer impregnated mesh is illustrated in FIGS. 6–14. Sheet 36b is a woven mesh of fibers 37b impregnated with a thin film of elastomeric material 38b. As shown in FIGS. 7–11, sheet 36b is folded over and placed in the desired position in mold 50. An elastomer, preferably of the same composition as the elastomer impregnating the sheet, is then injected into the mold and allowed to cure, i.e., harden, thus embedding and securing a portion of sheet 36b in the formed cushion 32b. The formed cushion 32b is then removed from mold 50 and bonded or otherwise secured to attaching member 34b, as shown in FIG. 12. The mesh is cut at the desired height above the cushion surface to form the completed pad shown in FIG. 13. As in the previous method, a preferred height is 0.05 inches above the cushion surface. An adhesive, such as a cyanoacrylate, for example LOCTITE 406, can be used to secure the cushion to the attaching member.

Figure 10:
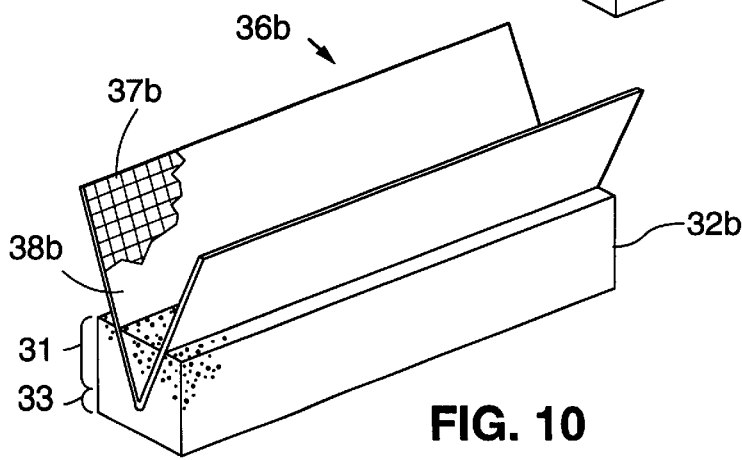
FIG. 10 is a perspective view of an assembled cushion according to the present invention.
Figure 11:
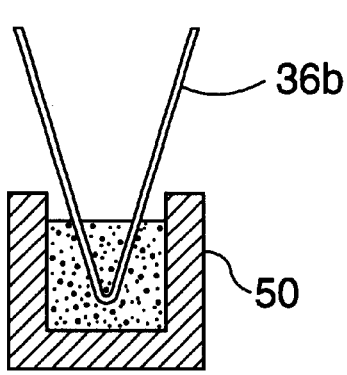
FIG. 11 is a cross-sectional view of the assembly of FIG. 9 taken along line 11—11 of FIG. 9.

As shown in FIG. 10, the formed cushion 32b has a clamping region 31 that is reinforced by the embedded mesh and a backing region 33 that supports the clamping region. Ideally, the mesh is embedded in the cushion to a depth such that the clamping region comprises the majority of the cushion. The embedded mesh functions to reinforce and stabilize the clamping region, while the clamping region, in turn, stabilizes and orients the mesh at the desired position relative to the cushion surface. Again it is preferred that elastomer 38b itself is of a softer resiliency relative to the mesh fibers.

Figure 13:
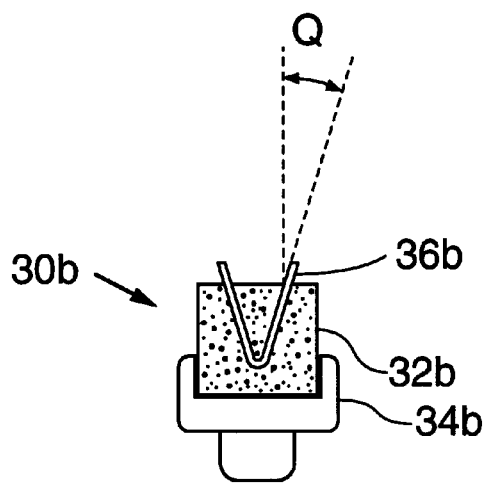
FIG. 13 is an end view of a cushion according to the present invention secured to an attaching member.
Figure 14:
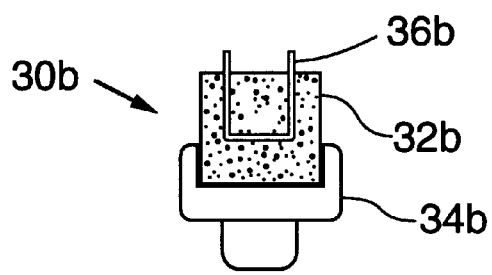
FIG. 14 is an end view of a cushion according to the present invention secured to an attaching member, with the mesh in a different configuration.

In the embodiment depicted in FIG. 13, the sheet 36b extends from cushion 32b at an angle Q from vertical relative to the cushion surface. The preferred angle Q is between 0 to 20 degrees from vertical relative to the surface of cushion 32b in either direction away from or toward the pad center. The sheet can also extend upward in a generally vertical direction relative to the surface of cushion 32b, as shown in the embodiment depicted in FIG. 14.

Although only certain embodiments have been illustrated and described, those having ordinary skill in the art will understand that the invention is not intended to be limited to the specifics of these embodiments, but rather is defined by the accompanying claims.

We claim:

1. A pad for attachment to a jaw of a jaw-type occlusion device comprising:
    an elastomeric cushion having a clamping surface; and
    an elastomer impregnated mesh embedded in said cushion and having portions thereof exposed at the clamping surface for engagement with a vessel.
2. The pad of claim 1 wherein said mesh is adapted to partially penetrate adventitial layers of the vessel upon engagement thereof for restricting movement of outer adventitial layers relative to inner vessel layers.
3. The pad of claim 1 wherein said mesh comprises woven fibers formed of a material that is resiliently deflectable and said cushion is formed of a material that is softer and more easily deflectable than said fiber material.
4. The pad of claim 1 wherein said mesh comprises woven fibers selected from the group consisting of nylon, polyester and polypropylene.
5. The pad of claim 1 wherein said cushion comprises silicone.
6. The pad of claim 1 wherein said elastomer is a thermoplastic elastomer.
7. The pad of claim 1 wherein said elastomeric cushion is formed of the same elastomer as that impregnating the mesh.
8. A pad for attachment to a jaw of a jaw-type occlusion device comprising;
    an elastomeric cushion having a clamping surface for engagement with a vessel and mesh embedded in said cushion,
    whereby said cushion is reinforced and stabilized by said mesh.
9. A pad according to claim 8 wherein said cushion comprises:
    (a) a clamping region reinforced by said mesh, and
    (b) a backing region which supports said clamping region.
10. The pad of claim 8 wherein
    (a) said mesh comprises woven fibers formed of a material that is resiliently deflectable, and
    (b) said cushion is formed of a material that is softer and more easily deflectable than said fiber material.
11. The pad of claim 8 wherein said mesh comprises woven fibers selected from the group consisting of nylon, polyester and polypropylene.
12. The pad of claim 8 wherein said elastomer is a thermoplastic elastomer.
13. The pad of claim 8 wherein the cushion comprises silicone.
14. The pad of claim 8 wherein said elastomeric cushion is formed of the same elastomer as that impregnating the mesh.
15. A method of manufacturing a pad for attachment to a jaw of a jaw-type occlusion device, the method comprising the steps of:
    a) providing a woven mesh;
    b) providing a mold having an upper web forming section and a lower cushion forming section, said sections defining a mold space;
    c) placing said mesh in said mold so as to extend within said upper and lower sections;
    d) injecting an elastomer into the mold space;
    e) allowing the elastomer to harden to form a cushion; and
    f) removing the formed cushion from the mold.
16. The method of claim 15 further comprising the steps of:
    (a) placing the mesh in the mold with a portion of the mesh extending out of the upper section of the mold; and
    (b) cutting the mesh to remove the portion extending from the upper section.
17. The method of claim 16 wherein the mesh further comprises a tubular sleeve.
18. The method of claim 15 wherein the mesh comprises woven fibers selected from the group consisting of nylon, polyester and propylene.
19. The method of claim 15 wherein the elastomer is a thermoplastic elastomer.
20. The method of claim 15 wherein the elastomer comprises silicone.
21. A method of manufacturing a pad for attachment to a jaw of a jaw-type occlusion device, the method comprising the steps of:

a) providing a sheet of elastomer impregnated mesh;

b) forming an uncured mass of polymeric material;

c) embedding a first portion of the sheet in the uncured mass so that a second portion of the sheet extends therefrom;

d) curing the mass to form a pad with the second portion of the sheet extending therefrom.

22. The method of claim 21 wherein said mesh comprises woven fibers selected from the group consisting of nylon, polyester and propylene.

23. The method of claim 21 wherein said elastomer is a thermoplastic elastomer.

24. The method of claim 21 wherein said polymeric material comprises silicone.

25. The method of claim 24 wherein said embedding step further comprises injection molding the silicone around the first portion of the sheet and allowing the silicone to cure.

26. The method of claim 21 wherein said embedding step further comprises the step of orienting the sheets at an angle of between 0–20 degrees from vertical relative to the surface of the pad.

27. A pad for attachment to a jaw of a jaw-type occlusion device comprising:

an elastomeric cushion having a clamping surface; and an elastomer impregnated mesh embedded in said cushion and having portions thereof exposed at the clamping surface for engagement with a vessel, said mesh having flexible fibers having portions extending from the surface of the cushion, and an elastomer forming a web between said portions.

28. The pad of claim 27 wherein said fibers terminate in distal ends spaced from the surface of the cushion.

29. The pad of claim 28 wherein the distal ends of the fibers are exposed through the elastomer and are coterminous with the web.

30. The pad of claim 29 wherein the elastomer is adapted to partially deflect upon engagement with the vessel to expose the distal ends of the fibers.

31. The pad of claim 27 wherein said elastomeric cushion is formed of the same elastomer as that impregnating the mesh.

32. A pad for attachment to a jaw of a jaw-type occlusion device comprising:

an elastomeric cushion; and elastomer impregnated mesh embedded in said cushion, a portion of which extends from a surface of said cushion, whereby said cushion is reinforced and stabilized by said mesh and said mesh is stabilized and oriented by said cushion.

33. The pad of claim 32 wherein said mesh comprises:

(a) flexible fibers having portions extending from the surface of the cushion; and, (b) an elastomer forming a web between said portions.

34. The pad of claim 33 wherein said fibers terminate in distal ends spaced from the surface of the cushion.

35. The pad of claim 34 wherein the distal ends of the fibers are exposed through the elastomer and are coterminous with the web.

36. The pad of claim 35 wherein the elastomer is adapted to partially deflect upon engagement with the vessel to expose the distal ends of the fibers.

37. A pad according to claim 32 wherein said cushion comprises (a) a clamping region reinforced by said mesh, and (b) a backing region which supports said clamping region.

38. The pad of claim 32 wherein (a) said mesh comprises woven fibers formed of a material that is resiliently deflectable, and (b) said cushion is formed of a material that is softer and more easily deflectable than said fiber material.

39. The pad of claim 32 wherein said mesh comprises woven fibers selected from the group consisting of nylon, polyester and polypropylene.

40. The pad of claim 32 wherein said elastomer is a thermoplastic elastomer.

41. The pad of claim 32 wherein the cushion comprises silicone.

42. The pad of claim 32 wherein said elastomeric cushion is formed of the same elastomer as that impregnating the mesh.

* * * * *